United States Patent [19]

Watkins et al.

[11] 4,054,664

[45] Oct. 18, 1977

[54] TRIAZOLE INSECTICIDES

[75] Inventors: Thomas I. Watkins; David M. Weighton, both of Nottingham, England

[73] Assignee: The Boots Company Limited, Nottingham, England

[21] Appl. No.: 594,372

[22] Filed: July 8, 1975

[30] Foreign Application Priority Data

July 8, 1974 United Kingdom ............... 30169/74

[51] Int. Cl.² ............................................... A01N 9/22
[52] U.S. Cl. .................................. 424/269; 260/308 R
[58] Field of Search ..................... 424/269; 260/308 R

[56] References Cited

U.S. PATENT DOCUMENTS

| 3,308,131 | 3/1967 | McKusick | 260/247.2 A |
|---|---|---|---|
| 3,862,125 | 1/1975 | Hoffman et al. | 424/269 |

Primary Examiner—V. D. Turner
Attorney, Agent, or Firm—Lawrence Rosen; E. Janet Berry

[57] ABSTRACT

1(2)-(N,N-disubstituted carbamoyl)-3,5-substituted-1,2,4-triazoles, useful as insecticidal compounds, and their preparation, are described.

6 Claims, No Drawings

TRIAZOLE INSECTICIDES

This invention relates to new chemical compounds having insecticidal activity and to their use as insecticides In U.S. Pat. No. 3,308,131 there is described a group of 1,2,4-triazoles of the general formulae

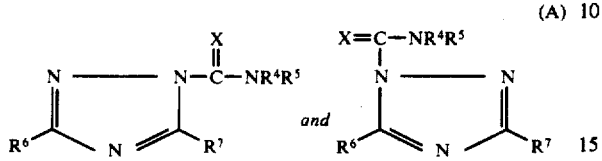

wherein X is oxygen or sulphur, $R^4$ and $R^5$ are aliphatic groups which together contain up to 14 carbon atoms and which may be joined to form a heterocyclic ring with the carbamoyl nitrogen atom, and $R^6$ and $R^7$, which together contain up to 14 carbon atoms, are free from aliphatic unsaturation and are selected from hydrogen, halogen, sulphonyl, mercapto, cyano, hydrocarbyl, halohydrocarbyl, nitrohydrocarbyl, hydrocarbyloxycarbonylhydrocarbyl, hydrocarbylsulphonyl, hydrocarbylmercapto, nitrohydrocarbylmercapto, halohydrocarbylmercapto, aminohydrocarbylmercapto and hydrocarbyloxyhydrocarbyl. These compounds are said to be insecticides and to possess analgesic properties.

We have now discovered a small group of new compounds within the general disclosure of this patent specification which have unusual properties. They are exceptionally effective insecticides and, in particular, we have found that compounds within the present small group are more active against a wide range of insects then compounds specifically described in U.S. Pat. No. 3,308,131. Furthermore, the compounds of the present group have a particularly valuable degree of activity against a variety of economically important insects such as the diamond back moth and other insects that cause serious and widespread damage to crops.

The compounds of the invention can be represented by the formulae

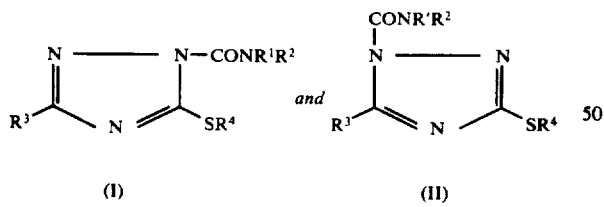

in which $R^1$ is methyl $R^2$ is methyl or ethyl, $R^3$ is isopropyl, s-butyl or t-butyl, and $R^4$ is methy, ethyl, propyl, vinyl prop-2-ynyl, but-2-enyl or 2-haloallyl, provided that when $R^4$ is propyl, $R^3$ is isopropyl or s-butyl and when $R^4$ is but-2-enyl $R^3$ is t-butyl.

These compounds have high activity against insects such as the larvae of the diamond back moth (*Plutella maculipennis*) and other insects of the order Lepidoptera for example the larvae of the codling moth (*Cydia pomonella*) and caterpillars such as for example those of the cabbage white butterfly (*Pieris brassicae*). They are also active against dipterous insects for example the cabbage root fly *Erioischia brassicae*, the house fly (*Musca domestica*) and mosquito larvae (for example *Aedes aetypti*) and against insects of the order Coleoptera for example the mustard beetle (*Phaedon Cochleariae*) and grain weevil (*Stitophilus granaria*). In addition other insect species such as aphids for example (*Megoura viciae*) and cockroach (*Blattella germanica*) can be controlled by their use.

The compounds of the invention can exist in isomeric forms. As usually prepared the compounds consist of a mixture of the two isomers indicated by formulae I and II above, with the exception of the compound in which $R^3$ is t-butyl and $R^4$ is methyl which is prepared is substantially pure form and is believed to be the structure indicated by formula I. The latter compound is designated 1-N,N-dimethylcarbamoyl-3-t-butyl-5-methylthio-1,2,4-triazole, whilst the remaining compounds are designated 1(2)-N,N-dimethylcarbamoyl-1,2,4-triazoles. In all cases the pairs of isomers can be separated by conventional methods such as for example chromatography, but, as the isomeric mixtures are of very valuable insecticidal activity, we generally find that there is no advantage in separating the isomers. The activity of the isomers of any one compound may differ and in some cases the activity of one isomer may be negligible: pure isomers lacking insecticidal activity form no part of the present invention. The isomers of formula I are thought in general to be the more active.

Specific examples of compounds according to the invention are:

1-N,N-dimethylcarbamoyl-3-t-butyl-5-methylthio-1,2,4-triazole

1(2)-N,N-dimethylcarbamoyl-3-isopropyl-5-methylthio-1,2,4-triazole

1(2)-N,N-dimethylcarbamoyl-3-isopropyl-5-ethylthio-1,2,4-triazole

1(2)-N,N-dimethylcarbamoyl-3-isopropyl-5-propylthio-1,2,4-triazole

1(2)-N,N-dimethylcarbamoyl-3s-butyl-5-methylthio-1,2,4-triazole

1(2)-N,N-dimethylcarbamoyl-3-s-butyl-5-ethylthio-1,2,4-triazole

1(2)-N,N-dimethylcarbamoyl-3-s-butyl-5-propylthio-1,2,4-triazole

1(2)-N,N-dimethylcarbamoyl-3-t-butyl-5-ethylthio-1,2,4-triazole

1(2)-N,N-dimethylcarbamoyl-3-isopropyl-5-prop-2-ynylthio-1,2,4-triazole

1(2)-N,N-dimethylcarbamoyl-3-t-butyl-5-prop-2-ynylthio-1,2,4-triazole

1(2)-N,N-dimethylcarbamoyl-3-t-butyl-5-but-2-enylthio-1,2,4-triazole

1(2)-N,N-dimethylcarbamoyl-3-s-butyl-5-prop-2-ynylthio-1,2,4-triazole

1(2)-N,N-dimethylcarbamoyl-3-t-butyl-5-vinylthio-1,2,4-triazole

1(2)-N,N-dimethylcarbamoyl-3-t-butyl-5-(2-chloroallythio)-1,2,4-triazole

1(2)-N,N-dimethylcarbamoyl-3-t-butyl-5-(2-bromoallylthio)-1,2,4-triazole

1(2)-N,N-dimethylcarbmoyl-3-isopropyl-5-(2-chloroallylthio)-1,2,4-triazole

1(2)-N,N-dimethylcarbamoyl-3-s-butyl-5-vinylthio-1,2,4-triazole

1(2)-N,N-dimethylcarbamoyl-3-isopropyl-5-vinylthio-1,2,4-triazole

1(2)-N,N-dimethylcarbamoyl-3-s-butyl-5-(2-chloroallylthio)-1,2,4-triazole

1(2)-N-ethyl-N-methylcarbamoyl-3-t-butyl-5-prop-2-ynylthio-1,2,4-triazole

Most suitable both $R^1$ and $R^2$ are methyl, and a preferred group of compounds is of formulae I and II in which $R^1$ and $R^2$ are methyl, $R^3$ is isopropyl, s-butyl or t-butyl and $R^4$ is methyl, ethyl, propyl vinyl, prop-2-ynyl or but-2-enyl. A further preferred group of compounds is of formulae I and II in which $R^1$ and $R^2$ are methyl, $R^3$ is isopropyl, s-butyl, or t-butyl and $R^4$ is methyl, ethyl, propyl or prop-2-ynyl. Of the compounds listed above 1-N,N-dimethylcarbamoyl-3-t-butyl-5-methylthio-1,2,4-triazole is especially suitable because of its activity against a wide range of insects.

The invention also includes an insecticidal composition comprising an insecticially active compound of formula I or II and an inert diluent. More than one compound of the invention can, of course, be included in the composition, and the diluent can be a solid or liquid, optionally together with a surface-active agent for example a dispersing agent, emulsifying agent or wetting agent.

One or more additional pesticides such as for example compounds known to possess acaricidal or insecticidal activity can be added to the composition of the invention to enhance or widen the spectrum of its acitivity. Examples include organochlorine compounds such as for example DDT, benzene hexachloride or dicofol; organophosphorus compounds such as for example, fenitrothion, azinphos-methyl, demeton or dimethoate; and carbamates such as for example carbaryl.

The composition of the invention can take any of the forms known for the formulation of insecticidal compounds, for example it can be in the forms of a solution, an aqueous dispersion, an aqueous emulsion, an emulsifiable concentrate, a dispersible powder, a dusting powder or granules. Thus it can be in a suitable form for direct application as in insecticide or as a concentrate requiring dilution with an appropriate quantity of water or other diluent before application.

As a dispersion the composition comprises a compound of the invention dispersed in an aqueous medium. It is often convenient to supply the consumer with a concentrate which diluted with water forms a dispersion of the desired concentration and can be provided in, for example, any of the following forms. It can be a dispersible solution which comprises a compound of the invention dissolved in a water-miscible solvent with the addition of a dispersing agent, or a dispersible powder comprising a compound of the invention and a dispersing agent. A further alternative comprises a compound of the invention in the form of a finely ground powder is association with a dispersing agent and intimately mixed with water to give a paste or cream which can if desired by added to an emulsion of oil in water to give a dispersion of active ingredient in an aqueous oil emulsion.

An emulsion comprises a compound of the invention dissolved in a water-immiscible solvent which is formed into an emulsion with water in the presence of an emulsifying agent. An emulsion of the desired concentration can be formed from a concentrated stock emulsion that comprises a compound of the invention in combination with an emulsifying agent, water and water-immiscible solvent. Alternatively the consumer can be supplied with an emulsifiable concentrate comprising a solution of a compound of the invention in a water-immiscible solvent containing an emulsifying agent.

A dusting powder comprises a compound of the invention intimately mixed and ground with a solid pulverulent diluent, for example, kaolin.

A granular solid comprises a compound of the invention associated with similar diluents to those employed in dusting powders but the mixture is granulated by known methods. Alternatively the active ingredient can be absorbed or adsorbed on a pre-formed granular diluent for example fuller's earth, attapulgite or limestone grit.

The concentration of the active ingredient in a composition intended for direct application is preferably within the range of 0.001 to 10 percent by weight of the composition, more especially within the range of 0.005 to 5 percent by weight. In a concentrate the amount of active ingredient can vary widely for example it can comprise from 5 to 95 percent by weight of the composition.

As previously described the compounds of the invention have exceptional activity as insecticides and accordingly the invention includes a method of combating insects which comprises applying a compound of the invention to the locus of the insects, that is, the insects or their habitat. The compound of the invention can either be applied on its own or more preferably as one of the compositions described above.

Many of the insects which the compounds of the invention are active against, for example those of the order Lepidoptera and dipterous insects, attack plant life and a preferred method of the invention is one for protecting plants from attack by insects by applying a compound of the invention to the locus of the plants, that is, the plants or their surroundings. For instance the diamond back moth, cabbage white butterfly and cabbage root fly attack vegetable crops such as brassicas; the codling moth is a pest on fruit crops such as for example apple trees; and aphids damage a wide variety of crops including, for example, ornamental plants such as roses and crops such as fruit trees, leguminous crops, potatoes, hops, sugar beet, cotton, maize, rice and tobacco.

As described above the compounds of the invention are especially active against the larvae of the diamond back moth (*Plutella maculipennis*) and a preferred group of compounds possessing activity of this kind is that of formulae I and II in which $R^1$ and $R^2$ are methyl, $R^3$ is isopropyl, s-butyl or t-butyl and $R^4$ is methyl ethyl, propyl vinyl, prop-2-ynyl or but-2-enyl. These compounds are therefore expecially suitable for use in a method of combating the insect *Plutella maculipennis* which comprises applying the compound to the locus of this insect.

A group of compounds within formulae I and II that is of particular use against the cabbage white butterfly (*Pieris brassicae*) is that in which $R^1$ and $R^2$ are methyl, $R^3$ is isopropyl or t-butyl and $R^4$ is methyl prop-2-ynyl or but-2enyl and accordingly the invention includes a method of combatting the insect Pieris brassicae which comprises applying one of these compounds to the locus of this insect. A further group of compounds of particular activity against cabbage root fly (*Erioischia brassicae*) is of formulae I and II in which $R^1$ and $R^2$ are methyl, $R^3$ is isopropyl or t-butyl, $R^4$ is methyl, propyl, prop-2-ynyl, but-2-enyl or 2-haloallyl.

Direct treatment by for example spraying or dusting the plants infested with insects is often the preferred method but the active compound can also be applied to the soil in which plants are grown as granules, or as a root drench. In such instances the active compound is absorbed by the roots of the plant and confers protection from the insects. The quantity of active compound applied can vary widely depending on the particular circumstances and usually the amount is in the range of from 0.005 to 10 lb./acre, more especially from 0.01 to 5 lb./acre.

In the case of insects such as cockroach, beetle, house fly and weevil all of which spoil stored products such as for example grain, root crops and foodstuffs, the active compound can be sprayed or dusted on to the stored product. Alternatively, the container or store-house can be treated by spraying or dusting the walls and floor or by fumigation. When spraying or dusting the container or store-house the rate of application of active compound is preferably from 0.25 to 50 ounces per 1,000 square feet and especially from 1 to 15 ounces per 1,000 square feet.

The compounds of the invention can be prepared by a process which comprises reacting a triazole of the formula

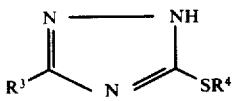

(III)

with a carbamoyl halide of the formula $R^1R^2NCOZ$ (IV) in which $R^1$, $R^2$, $R^3$ and $R^4$ are as defined in formulae I and II above and Z is halogen, for example bromine or preferably chlorine. The reaction is most suitably carried out in the presence of an inert organic liquid as the reaction medium which is preferably a solvent for the reactants. Advantageously the reaction is effected in the presence of a suitable acid-binding agent, for example a tertiary amine, pyridine or an alkali metal carbonate, in order to absorb the hydrogen halide produced by the reaction. Alternatively it can be carried out by first forming an alkali metal derivative of the triazole, for example an N-sodio-derivative, by reaction with an alkali-metal hydride, and subsequently reacting with the carbamoyl halide. In preparing the compounds of the invention the reactants are preferably reacted together at a temperature of from 40° to 200° C for example from 50° to 150° C.

The novel triazole reactants of formula III can be prepared by, for example, treating the appropriate acyl thiosemicarbazide of formula $R^3CONHNHCSNH_2$ with a ring closing agent such as for example aqueous sodium hydroxide, sodium methoxide in methanol or piperidine. The resulting 3-alkyl-1,2,4-triazole-5-thiol can be reacted with a halide of the formula $R^4Z$ in which Z is halogen, in the presence of a strong base to give the compound of formula III. When, however, the group $R^4$ is vinyl the compound of formula III is preferably prepared by reacting the 3-alkyl-1,2,4-triazole-5-thiol with dihaloethane, for example an excess of dichloroethane or substantially equimolar proportions of 1-bromo-2-chloroethane, followed by removal of hydrogen halide in the presence of strong base.

The carbamoyl halide of formula IV is prepared by reacting an amine of the formula $R^1R^2NH$ with a carbonyl halide of the formula $COZ_2$ in which Z is halogen, preferably chlorine, in accordance with known methods.

The invention is illustrated by the following examples.

EXAMPLE 1

This example illustrates the preparation of compounds according to the invention.

To a stirred suspension of 7.2 g. 3-isopropyl-5-prop-2-ynylthio-1,2,4-triazole in 72 ml. acetone was added 6.1 g. anhydrous potassium carbonate followed by 4.7 g. N,N-dimethylcarbamoyl chloride. The mixture was stirred and boiled under reflux for 8 hours. The reaction mixture was cooled and then poured into one liter of ice-water mixture and an oil separated which was extracted with three 200 ml. portions of chloroform. The extracts were dried over anhydrous magnesium sulphate and distilled to give the product 1(2)-N,N-dimethylcarbamoyl-3-isopropyl-5-prop-2-ynylthio-1,2,4-triazole, boiling point 134°-136° C. at 0.05 mm.

The 3-isopropyl-5-prop-2-ynylthio-1,2,4-triazole starting material was prepared in the following way.

200 g. Isobutyryl chloride at a temperature of about $-5°$ C. was added dropwise over a half hour period to a stirred suspension of 171 g. thiosemicarbazide in 1.5 liter dry pyridine. The mixture was stirred overnight at room temperature and then evaporated at 35°-40° C. to a clear yellow viscous oil. After dissolving the oil in 3 liters of methanol it was treated with 950 ml. sodium methoxide solution (11.4 percent w/w) and stirred under reflux for twelve hours. The methanol was removed by distillation, the residual semi-solid dissolved in 1 liter hot water, treated with charcoal and filtered through diatomaceous earth. When cooled and acidified with 200 ml. concentrated hydrochloric acid a white solid separated. It was filtered off, washed with iced water and dried under vacuum. The solid was 5-mercapto-3-isopropyl-1,2,4-triazole, melting point 184°-186° C.

11.9 g. Prop-2-ynyl bromide was added to a solution of 14.3 g. 5-mercapto-3-isopropyl-1,2,4-triazole in sodium methoxide solution (2.3 g. sodium dissolved in 200 ml. methanol). Then the solution was boiled under reflux for 2 1/2 hours. The solvent was evaporated under reduced pressure from the steam bath and the residual solid triturated with 500 ml. cold water, filtered off and dried under vacuum to give 3-isopropyl-5-prop-2-ynylthio-1,2,4-triazole which was purified by recrystallisation in the presence of charcoal, from petroleum ether (boiling point 80°-100° C.). The melting point of the product was 91°-92° C.

The following compounds were made in a similar manner.

1(2)-N,N-dimethylcarbamoyl-3-t-butyl-5-prop-2-ynylthio-1,2,4-triazole, b.p. 127°-128° C./0.3 mm.
1(2)-N,N-dimethylcarbamoyl-3-s-butyl-5-prop-2-ynylthio-1,2,4-triazole, b.p. 120°-123° C./0.3 mm.
1(2)-N,N-dimethylcarbamoyl-3-t-butyl-5-(2-bromoallylthio)-1,2,4-triazole, b.p. 139°-148° C./0.25 mm.
1(2)-N,N-dimethylcarbamoyl-3-isopropyl-5-(2-chloroallylthio)-1,2,4-triazole, b.p. 135° C./0.4 mm.
1(2)-N-ethyl-N-methylcarbamoyl-3-t-butyl-5-prop-2-ynylthio-1,2,4-triazole, b.p. 118°-119° C./0.1 mm.
1(2)-N,N-dimethylcarbamoyl-3-s-butyl-5-(2-chloroallylthio)-1,2,4-triazole, b.p. 158°-164° C./0.2 mm.
1(2)-N,N-dimethylcarbamoyl-3-isopropyl-5-(2-bromoallylthio)-1,2,4-triazole, b.p. 157° C./0.25 mm.

In the course of preparing the above carbamoyl-triazole compounds the following triazole intermediates were isolated.

3-t-butyl-5-prop-2-ynylthio-1,2,4-triazole, m.p. 125° C.

3-s-butyl-5-prop-2-ynylthio-1,2,4-triazole, b.p. 150° C./0.5 mm.

3-t-butyl-5-(2-bromoallylthio)-1,2,4-triazole, m.p. 144°-145° C.

3-isopropyl-5-(2-chloroallylthio)-1,2,4-triazole, m.p. 84°-86° C.

EXAMPLE 2

This example illustrates the preparation of compounds according to the invention.

To a stirred suspension of 60.5 g. sodium hydride (50 percent oil dispersion) in 300 ml. dry tetrahydrofuran was added a solution of 171 g. 3-t-butyl-5-methylthio-1,2,4-triazole in 1 liter dry tetrahydrofuran. The mixture was stirred under reflux for two hours. 154 g. Dimethylcarbamoyl chloride was then added dropwise and the reaction mixture stirred under reflux for a further five hours. After cooling the mixture to room temperature it was filtered through Celite, a diatomaceous earth, and the tetrahydrofuran distilled off. The residual oil was dissolved in methylene chloride the solution washed with ice cold 0.5N sodium hydroxide, ice cold 0.5N hydrochloric acid and water until the washings were neutral and then dried over magnesium sulphate. Removal of the solvent and distillation of the residue gave a colourless oil, 1-N,N-dimethylcarbamoyl-3-methylthio-5-t-butyl-1,2,4-triazole, boiling point 119°-121° C. at 0.15 mm. The oil solidified on standing to give the solid product, melting point 49°-51° C.

The 3-t-butyl-5-methylthio-1,2,4-triazole starting material was prepared in the following way.

80.5 g. Pivaloyl chloride was added dropwise at a temperature of about −5° C. to a stirred suspension of 91 g. thiosemicarbazide in one liter dry pyridine. The mixture was stirred overnight and then evaporated at 30° C./30 mm. to a paste.

The paste was then treated with 400 ml. sodium methoxide solution (11.7 percent w/w) and two liters of dry methanol. After stirring under reflux overnight the reaction mixture was evaporated, dissolved in water, charcoaled and filtered through Celite, a diatomaceous earth. The filtrate was then acidified with concentrated hydrochloric acid and the cream coloured solid separated and was recrystallised from hot water, 3-t-butyl-5-mercapto-1,2,4-triazole, melting point 196°-197° C.

To a solution of 4.8 g. sodium methoxide in 250 ml. industrial methylated spirits was added 14 g. 3-t-butyl-5-mercapto-1,2,4-triazole. The mixture was heated and stirred until homogeneous when 18.96 g. methyl iodide was added followed by refluxing for a period of 3 1/2 hours. The solvent was distilled off and the residual liquor poured on to crushed ice. The white solid was filtered, dried and recrystallised from toluene, 3-t-butyl-5-methylthio-1,2,4-triazole, melting point 186°-187° C.

The following compounds were made in a similar manner

1(2)-N,N-dimethylcarbamoyl-3-isopropyl-5-methylthio-1,2,4-triazole, b.p. 123° C./0.6 mm.

1(2)-N,N-dimethylcarbamoyl-3-isopropyl-5-ethylthio-1,2,4-triazole, b.p. 126°-128° C./0.8 mm.

1(2)-N,N-dimethylcarbamoyl-3-isopropyl-5-propylthio-1,2,4-triazole, b.p. 103°-106° C./0.05 mm.

1(2)-N,N-dimethylcarbamoyl-3-s-butyl-5-methylthio-1,2,4-triazole, b.p. 129°-130° C./0.7 mm.

1(2)-N,N-dimethylcarbamoyl-3-s-butyl-5-ethylthio-1,2,4-triazole, b.p. 119.5°-120° C./0.3 mm.

1(2)-N,N-dimethylcarbamoyl-3-s-butyl-5-propylthio-1,2,4-triazole, b.p. 130°-131° C./0.4 mm.

1(2)-N,N-dimethylcarbamoyl-3-t-butyl-5-ethylthio-1,2,4-triazole, b.p. 120°-125° C./0.5 mm.

1(2)-N,N-dimethylcarbamoyl-3-t-butyl-5-(2-chloroallylthio)-1,2,4-triazole, b.p. 131°-135° C./4 mm.

In the course of preparing the above carbamoyl-triazole compounds the following triazole intermediates were made.

3-isopropyl-5-methylthio-1,2,4-triazole, m.p. 131°-132° C.

3-isopropyl-5-ethylthio-1,2,4-triazole, m.p. 103°-104° C.

3-isopropyl-5-propylthio-1,2,4-triazole, m.p. 81°-83° C.

3-s-butyl-5-methylthio-1,2,4-triazole, m.p. 73°-75° C.

3-s-butyl-5-ethylthio-1,2,4-triazole, m.p. 60°-61° C.

3-s-butyl-5-propylthio-1,2,4-triazole, m.p. ≡°-58° C.

3-t-butyl-5-ethylthio-1,2,4-triazole, m.p. 157° C.

3-t-butyl-5-(2-chloroallylthio)-1,2,4-triazole, m.p. 122°-123° C.

EXAMPLE 3

This example illustrates the preparation of 1(2)-N,N-dimethylcarbamoyl-3-t-butyl-5-but-2-enylthio-1,2,4-triazole.

To a stirred solution of 8 g. 3-t-butyl-5-but-2-enylthio-1,2,4-triazole in 100 ml. acetone was added 5.8 g. potassium carbonate followed by 4.5 g. carbamoyl chloride. The mixture was refluxed for five hours, cooled, filtered, and evaporated to an oil. On distillation in vacuo the product was collected, 1(2)-N,N-dimethylcarbamoyl-3-t-butyl-5-but-2-enylthio-1,2,4-triazole, boiling point 120°-123° C. at 0.15 mm.

The novel triazole intermediate used in the above preparation was made in the following way. 10 g. 3-t-Butyl-5-mercapto-1,2,4-triazole prepared as described in Example 2 was dissolved in a solution of 3.8 g. sodium methoxide in 100 ml. methanol and 9.5 g. crotyl bromide was added. After 5 hours refluxing, the mixture was evaporated and the residue triturated with an ether/water mixture. The ether layer was separated, washed with water, dried and evaporated to a solid which was recrystallised from a methanol/water mixture, 3-t-butyl-5-but-2-enylthio-1,2,4-triazole, melting point 138°-140° C.

EXAMPLE 4

This example illustrates the preparation of 1(2)-N,N-dimethylcarbamoyl-3-t-butyl-5-vinylthio-1,2,4-triazole.

To a stirred suspension of 3.66 g. 3-t-butyl-5-vinylthio 1,2,4-triazole in 25 ml. dry tetrahydrofuran was added 1.2 g. sodium hydride (50 percent oil dispersion). When the evolution of hydrogen has subsided 2.5 ml. dimethylcarbamoyl. chloride was added. Heat was evolved and after being allowed to remain at room temperature for a period of two hours the mixture was filtered and evaporated under reduced pressure. On distillation the liquid product was obtained, boiling point 107° C. at 0.16 mm.

The triazole reactant used in the above preparation was made in the following way.

31.4 g. 3-t-Butyl-1,2,4-triazole-5-thiol was dissolved in 180 ml. industrial methylated spirits containing 12.4 g. potassium hydroxide. 99 g. 1,2-Dichloroethane was added and after four days the insoluble matter removed. 5-(2-Chloroethylthio)-3-t-butyl-1,2,4-triazole was obtained from the solution by evaporation.

7 g. Potassium was dissolved in 250 ml. t-butanol by refluxing and 14.7 g. 5-(2-chloroethylthio)-3-t-butyl-1,2,4-triazole added to the cooled solution. The mixture was left overnight and then saturated with carbon dioxide to give a gelatinous precipitate of potassium carbonate. 100 ml. Water was added and the mixture separated in a funnel. Extraction of the aqueous layer with ethyl acetate and evaporation of this solvent in a crystallising basin on the steam bath gave a solid product, which was recrystallised from ethyl acetate, 3-t-butyl-5-vinylthio-1,2,4-triazole, melting point 177°–179° C.

The following compounds were made in a similar manner.

1(2)-N,N-dimethylcarbamoyl-3-s-butyl-5-vinylthio-1,2,4-triazole, b.p. 100° C./0.02 mm.

1(2)-N,N-dimethylcarbamoyl-3-isopropyl-5-vinylthio-1,2,4-triazole, b.p. 100° C./0.02 mm.

The corresponding triazole intermediates 3-s-butyl-5-vinylthio-1,2,4-triazole and 3-isopropyl-5-vinylthio-1,2,4-triazole were made but were not isolated as the pure product.

EXAMPLE 5

Granules containing 5% w/w of 1-N,N-Dimethylcarbamoyl-3-methylthio-5t-butyl-1,2,4-triazole were prepared by forming a solution of the compound in xylene together with 0.5% w/w calcium dodecylbenzenesulphonate and 0.5% w/w of a nonylphenolethylene oxide condensate containing an average of 14 molecules ethylene oxide per molecule of phenol, and impregnating granules of fuller's earth (mesh size 20/40 British Standard Sieve). The xylene was then evaporated from the impregnated granules.

Granules containing the following compounds were made in a similar manner.

1(2)-N,N-dimethylcarbamoyl-3-t-butyl-5-but-2-enylthio-1,2,4-triazole

1(2)-N,N-dimethylcarbamoyl-3-t-butyl-5-prop-2-ynylthio-1,2,4-triazole

1(2)-N,N-dimethylcarbamoyl-3-t-butyl-5-vinylthio-1,2,4-triazole

EXAMPLE 6

An emulsifiable concentrate suitable for dilution with water to form an aqueous emulsion was prepared from the following ingredients:

| 1-N,N-Dimethylcarbamoyl-3-methylthio-5-t-butyl-1,2,4-triazole | |
|---|---|
| | 25% w/v |
| Calcium dodecylbenzenesulphonate | 2.5% w/v |
| Nonylphenolpolyethoxyethanol* | 2.5% w/v |
| Isophorone | 20.0% volume |
| Xylene | to 100.0% volume |

*A nonylphenol-ethylene oxide condensate containing an average of 14 mols. ethylene oxide per mol. nonylphenol.

EXAMPLE 7

Emulsifiable concentrates suitable for dilution with water to form aqueous emulsions were prepared from the following ingredients:

| Compound | 25.0% w/v |
|---|---|
| Calcium dodecylbenzenesulphonate | 2.5% w/v |
| Nonylphenol polyethoxyethanol | 2.5% w/v |

| -continued | |
|---|---|
| Xylene | to 100.0% volume |

The following compounds were employed

1(2)-N,N-dimethylcarbamoyl-3-t-butyl-5-but-2-enylthio-1,2,4-triazole

1(2)-N,N-dimethylcarbamoyl-3-t-butyl-5-prop-2-ynylthio-1,2,4-triazole

1(2)-N,N-dimethylcarbamoyl-3-t-butyl-5-vinylthio-1,2,4-triazole

EXAMPLE 8

A dispersible powder was prepared from the following ingredients

| 1-N,N-Dimethylcarbamoyl-3-methylthio-5-t-butyl-1,2,4-triazole | |
|---|---|
| | 25.0% w/v |
| Dyapol PT* | 5.0% w/v |
| Sodium dioctylsulphosuccinate | 0.5% w/v |
| Silicic acid | 20.0% w/v |
| Kaolin | to 100.0% weight |

*Dyapol PT is the sodium salt of a sulphonated condensation product, of cresol, urea and formaldehyde.

EXAMPLE 9

This example illustrates the activity of the compounds of the invention against larvae of the diamond back moth (*Plutella maculipennis*).

Ten larvae were placed in a tube together with a square inch of cabbage leaf which had been dipped in the test solution and allowed to dry. After 24 hours untreated cabbage was added for food and after a further 24 hours an assessment was made of the mortality of the larvae.

Two replicates were carried out for each test compound and test solutions of varying concentrations employed so that an $LD_{50}$ value could be calculated.

Compounds prepared in Examples 1 to 4 were tested with the following results:

Table 1

| COMPOUND | | | | ACTIVITY $LD_{50}$ |
|---|---|---|---|---|
| $R^1$ | $R^2$ | $R^3$ | $R^4$ | p.p.m. |
| methyl | methyl | isopropyl | methyl | 160 |
| methyl | methyl | isopropyl | ethyl | 140 |
| methyl | methyl | isopropyl | propyl | 220 |
| methyl | methyl | s-butyl | methyl | 140 |
| methyl | methyl | s-butyl | ethyl | 220 |
| methyl | methyl | s-butyl | propyl | 320 |
| methyl | methyl | t-butyl | methyl | 100 |
| methyl | methyl | isopropyl | prop-2-ynyl | 87 |
| methyl | methyl | t-butyl | prop-2-ynyl | 33 |
| methyl | methyl | t-butyl | but-2-enyl | 220 |
| methyl | methyl | s-butyl | prop-2-ynyl | 270 |
| methyl | methyl | t-butyl | vinyl | 160 |
| methyl | methyl | s-butyl | vinyl | 160 |
| methyl | methyl | isopropyl | vinyl | <25 |
| ethyl | methyl | t-butyl | prop-2-ynyl | 68 |

Comparative Example

For the purposes of comparison, various 1,2,4-triazoles within the scope of formulae A disclosed in United States Patent Specification No. 3,308,131, but outside the scope of formulae I and II were tested by the method described in Example 9 and the $LD_{50}$ values (p.p.m.) are given below.

Table 2

|  | Plutella maculipennis |
|---|---|
| *1-dimethylcarbamoyl-3-methyl-1,2,4-triazole | >5000 |
| *1-dimethylcarbamoyl-3-chloro-1,2,4-triazole | >5000 |
| *1-dimethylcarbamoyl-3-bromo-1,2,4-triazole | >5000 |
| *1-dimethylcarbamoyl-3-methylthio-1,2,4-triazole | 2300 |
| *1-dimethylcarbamoyl-1,2,4-triazole | 1250 |
| *1(2)-dimethylthiocarbamoyl-3-methylthio-5-methyl-1,2,4-triazole | >5000 |
| *1(2)-diethylcarbamoyl-3-methylthio-5-methyl-1,2,4-triazole | >5000 |
| *1(2)-N-methyl-N-n-butylcarbamoyl-3-methylthio-5-methyl-1,2,4-triazole | >5000 |
| *1(2)-dimethylcarbamoyl-3-ethylthio-5-methyl-1,2,4-triazole | 1600 |
| *1-dimethylcarbamoyl-3-dodecylthio-5-methyl-1,2,4-triazole | >5000 |
| 1-dimethylcarbamoyl-3-n-hexylthio-1,2,4-triazole | >5000 |
| 1-dimethylcarbamoyl-3-cyclohexylthio-1,2,4-triazole | >5000 |
| 1-dimethylcarbamoyl-3-dodecylthio-1,2,4-triazole | >5000 |
| *1-dimethylcarbamoyl-3-undecyl-5-methylthio-1,2,4-triazole | >5000 |
| *1-dimethylcarbamoyl-3-benzylthio-5-methyl-1,2,4-triazole | >5000 |
| *1-dimethylcarbamoyl-3-phenyl-5-methylthio-1,2,4-triazole | >5000 |
| *1-dimethylcarbamoyl-3-p-nitrophenylthio-5-methyl-1,2,4-triazole | >5000 |
| 1-dimethylcarbamoyl-3-(2,4-dinitrophenylthio)-1,2,4-triazole | >5000 |
| *1-dimethylcarbamoyl-3,5-dimethyl-1,2,4-triazole | >5000 |
| *1-dimethylcarbamoyl-3-ethoxycarbonylmethylthio-5-methyl-1,2,4-triazole | >5000 |
| *1-dimethylcarbamoyl-3-(1-dimethylcarbamoyl-1,2,4-triazole-3-yldithio)-1,2,4-triazole | >5000 |
| *1-(4-methylpiperidinocarbonyl)-1,2,4-triazole | >5000 |
| *1(2)-pyrrolidinocarbonyl-3-methylthio-5-methyl-1,2,4-triazole | >5000 |
| 1(2)-diallylcarbamoyl-3-ethylthio-5-methyl-1,2,4-triazole | >5000 |
| 1-diallylcarbamoyl-3-(2-diethylaminoethylthio)-1,2,4-triazole | >5000 |
| 1-diallylcarbamoyl-3-methoxycarbonylmethylthio-1,2,4-triazole | >5000 |
| 1-di(cyanomethyl)carbamoyl-3-ethylthio-1,2,4-triazole | >5000 |
| *1-dimethylcarbamoyl-3-ethyl-5-methylthio-1,2,4-triazole | 1900 |
| *1-dimethylcarbamoyl-3-methyl-5-methylthio-1,2,4-triazole | 2200 |

Key
*indicates a compound specifically exemplified in U.S. Pat. Specification No. 3,308,131. Those compounds that are believed to have been obtained as a mixture of isomers are designated 1(2)- in the nomenclature of the carbamoyl group. The remaining compounds are believed to have been obtained substantially as the isomer given.

The results in Table 2 show that the prior art compounds are markedly inferior in their insecticidal activity to the compounds of the invention listed in Table 1. This marked superiority of the compounds of the invention is all the more surprising in view of their very close structural similarity with the prior art compounds.

EXAMPLE 10

This example illustrates the activity of compounds of the invention against larvae of the cabbage white butterfly (*Pieris brassicae*).

Ten larvae were placed in a tube together with a square inch of cabbage leaf which had been dipped in the test solution and allowed to dry. After 24 hours untreated cabbage was added for food and after a further 24 hours an assessment was made of the mortality of the larvae.

Two replicates were carried out for each of the following compounds prepared in Examples 1 to 3, at varying concentrations of test compound so that an $LD_{50}$ value could be calculated.

Table 3

| COMPOUND | | | | ACTIVITY $LD_{50}$ |
|---|---|---|---|---|
| $R^1$ | $R^2$ | $R^3$ | $R^4$ | p.p.m. |
| methyl | methyl | t-butyl | methyl | 43 |
| methyl | methyl | t-butyl | prop-2-ynyl | 27 |
| methyl | methyl | t-butyl | but-2-enyl | 27 |
| methyl | methyl | isopropyl | methyl | 59 |
| methyl | methyl | isopropyl | prop-2-ynyl | 31 |

EXAMPLE 11

This example illustrates the activity of compounds of the invention against the eggs of the cabbage root fly (*Erioischia brassicae*).

Ten eggs were placed in a solution containing the active compound in varying concentrations so that an $LD_{50}$ value could be calculated. The eggs were then stored for six days and the egg hatch then counted. Two replicates were carried out for each of the following compounds prepared in Examples 1 to 3.

Table 4

| COMPOUND | | | | ACTIVITY $LD_{50}$ |
|---|---|---|---|---|
| $R^1$ | $R^2$ | $R^3$ | $R^4$ | p.p.m. |
| methyl | methyl | t-butyl | methyl | 0.5 |
| methyl | methyl | t-butyl | prop-2-ynyl | 0.8 |
| methyl | methyl | t-butyl | but-2-enyl | 1.2 |
| methyl | methyl | t-butyl | 2-chloroallyl | 0.22 |
| methyl | methyl | t-butyl | 2-bromoallyl | 0.57 |
| methyl | methyl | isopropyl | 2-chloroallyl | 0.27 |
| methyl | methyl | isopropyl | propyl | 0.57 |
| methyl | methyl | s-butyl | 2-chloroallyl | 0.8 |
| methyl | methyl | isopropyl | 2-bromoallyl | 0.9 |

EXAMPLE 12

This example illustrates the activity of compounds of the invention against the larvae of the codling moth (*Cydia pomonella*).

An apple sprayed with test solution was allowed to dry and a perspex ring of 1 inch diameter was attached to the apple. Ten larvae were then placed on the apple surface and contained within the ring by means of a muslin covering. After five days an assessment of mortality was made by counting the number of strikes (i.e. the number of entry holes) made by the larvae.

Two replicates were carried out for each of the following compounds prepared in Examples 1 and 2, at varying concentrations test compound so that an $LD_{50}$ value could be calculated.

TABLE 5

| COMPOUND | | | | ACTIVITY $LD_{50}$ |
|---|---|---|---|---|
| $R^1$ | $R^2$ | $R^3$ | $R^4$ | p.p.m. |
| methyl | methyl | t-butyl | methyl | 50 |
| methyl | methyl | s-butyl | methyl | 14 |
| methyl | methyl | isopropyl | methyl | 37 |
| methyl | methyl | isopropyl | ethyl | <10 |
| methyl | methyl | s-butyl | ethyl | 18 |
| methyl | methyl | isopropyl | propyl | <10 |

TABLE 5-continued

| COMPOUND | | | | ACTIVITY LD$_{50}$ |
|---|---|---|---|---|
| R$^1$ | R$^2$ | R$^3$ | R$^4$ | p.p.m. |
| methyl | methyl | s-butyl | propyl | 10 |
| methyl | methyl | t-butyl | ethyl | 24 |

EXAMPLE 13

This example illustrates the activity of compounds of the invention against the aphid *Megoura viciae*.

Broad bean plants 3 to 5 cm. high were infested with aphids and then sprayed with an aqueous dispersion containing varying concentrations of test compound. Each plant was kept under a lamp glass for 24 hours and then examined. In this way an LD$_{50}$ value for the compounds was calculated. The aphid populations on control plants that had been treated with an aqueous spray not containing any test compound were unaffected.

Table 6

| COMPOUND | | | | ACTIVITY LD$_{50}$ |
|---|---|---|---|---|
| R$^1$ | R$^2$ | R$^3$ | R$^4$ | p.p.m. |
| methyl | methyl | t-butyl | methyl | 0.5 |
| methyl | methyl | t-butyl | prop-2-ynyl | 1.1 |
| methyl | methyl | t-butyl | but-2-enyl | 0.19 |
| methyl | methyl | t-butyl | 2-chloroallyl | 1.6 |
| methyl | methyl | t-butyl | 2-bromoallyl | 0.66 |
| methyl | methyl | s-butyl | methyl | 0.32 |
| methyl | methyl | isopropyl | methyl | 1.1 |
| methyl | methyl | isopropyl | prop-2-ynyl | 1.5 |
| methyl | methyl | isopropyl | 2-chloroallyl | 1.2 |
| methyl | methyl | s-butyl | ethyl | 0.66 |
| methyl | methyl | isopropyl | propyl | 1.6 |
| methyl | methyl | s-butyl | propyl | 0.86 |
| methyl | methyl | t-butyl | ethyl | 0.71 |
| methyl | methyl | t-butyl | vinyl | 0.61 |

We claim:

1. A method of controlling insect larvae which comprises applying to the locus of the larvae a larvicidally effective amount of a compound selected from the group consisting of triazoles of the formulae

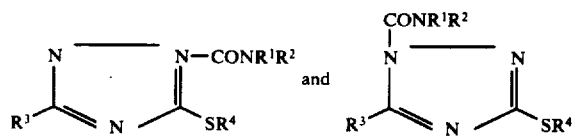

in which R$^1$ and R$^2$ are methyl, R$_3$ is selected from the group consisting of isopropyl, s-butyl, and t-butyl and R$^4$ is selected from the group consisting of methyl, ethyl, propyl, vinyl prop-2-ynyl, and but-2-enyl, provided that when R$^4$ is propyl R$^3$ is selected from the group consisting of isopropyl and s-butyl and when R$^4$ is but-2-enyl R$^3$ is t-butyl.

2. A method of protecting plants from larvae of the insect species of the group consisting of dipterous insects and insects of the order Lepidoptera which comprises applying to the locus of the plants a larvicidally effective amount of a compound selected from the group consisting of triazoles of the formulae

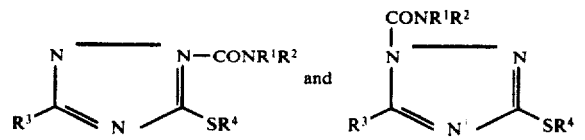

in which R$^1$ and R$^2$ are methyl, R$_3$ is selected from the group consisting of isopropyl, s-butyl, and t-butyl and R$^4$ is selected from the group consisting of methyl, ethyl, propyl, vinyl, prop-2-ynyl, and but-2-enyl, provided that when R$^4$ is propyl R$^3$ is selected from the group consisting of isopropyl and s-butyl and when R$^4$ is but-2-enyl R$^3$ is t-butyl.

3. A method of controlling larvae of the insect Plutella maculipennis which comprises applying to locus of the larvae a larvicidally effective amount of a compound selected from the group consisting of triazoles of the formulae

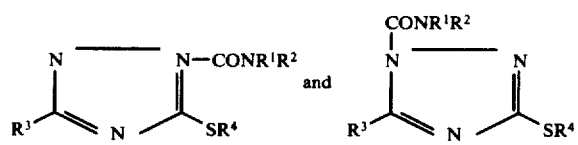

in which R$^1$ and R$^2$ are methyl, R$^3$ is selected from the group consisting of isopropyl, s-butyl, and t-butyl and R$^4$ is selected from the group consisting of methyl, ethyl, propyl, vinyl, prop-2-ynyl, and but-2-enyl, provided that when R$^4$ is selected from the group consisting of isopropyl and s-butyl and when R$^4$ is but-2-enyl R$^3$ is t-butyl.

4. A method of controll-larvae of the insect *Pieris brassicae* which comprises applying to the locus of the larvae a larvicidally effective amount of a compound selected from the group consisting of triazoles of the formulae

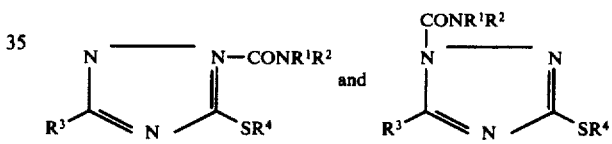

in which R$^1$ and R$^2$ are methyl, is selected from the group consisting of isopropyl and t-butyl, R$^4$ is selected from the group consisting of methyl, prop-2-ynyl and but-2-enyl.

5. A method of controll-larvae of the insect *Erioschia brassicae* which comprises applying to the locus of the larvae a larvicidally effective amount of a compound selected from the group consisting of triazoles of the formulae

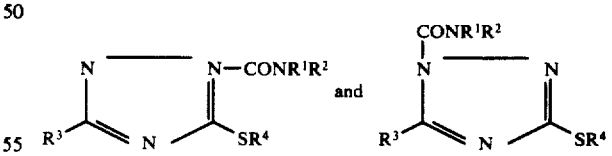

in which R$^1$ and R$^2$ are methyl, R$^3$ is selected from the group consisting of isopropyl and t-butyl, R$^4$ is selected from the group consisting of methyl, propyl, prop-2-ynyl, and but-2-enyl.

6. A method of protecting from larvae of the insect species of the group consisting of dipterous insects and insects of the order Lepidoptera which comprises applying a larvicidally effective amount of 1-N,N-dimethylcarbamoyl-3-t-butyl-5-methylthio-1,2,4-triazole to the locus of plants.

* * * * *